United States Patent [19]

Smith et al.

[11] Patent Number: 4,925,853

[45] Date of Patent: May 15, 1990

[54] BENZIMIDAZOLES AS 5-LIPOXYGENASE INHIBITORS

[75] Inventors: Stephen A. Smith, Hertfordshire; Roger E. Markwell, Essex, both of England

[73] Assignee: Beecham Group PLC, Brentford, England

[21] Appl. No.: 290,858

[22] Filed: Dec. 28, 1988

Related U.S. Application Data

[63] Continuation of Ser. No. 766,275, Aug. 16, 1985, abandoned.

[30] Foreign Application Priority Data

Aug. 17, 1984 [GB]  United Kingdom ............... 8420919
Jun. 4, 1985 [GB]  United Kingdom ............... 8514016

[51] Int. Cl.$^5$ ................. A61K 31/44; A61K 31/415
[52] U.S. Cl. ........................... 514/338; 514/394; 548/325; 548/327; 548/330; 548/331; 548/333; 548/334
[58] Field of Search ........................... 514/394, 338

[56] References Cited

U.S. PATENT DOCUMENTS 1,314,928  9/1919  Andrews ........................... 564/305

FOREIGN PATENT DOCUMENTS 8503982  1/1983  Australia.
1642883  1/1984  Australia.

OTHER PUBLICATIONS

Beckett, A., et al., *J. Pharm. Pharmacol.*, 1955, 7, 717 and 722.
Hofmann, K., *Imidazole and its Derivatives*, Part I, Interscience, New York, 1953, pp. 258-259.

Primary Examiner—Richard A. Schwartz
Attorney, Agent, or Firm—James F. Haley, Jr.; Leon R. Yankwich

[57] ABSTRACT

Compounds of the general formula I

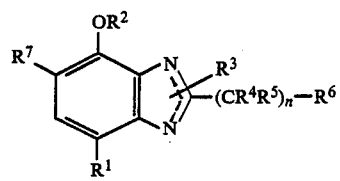

or pharmaceutically acceptable salts or solvates thereof, in which $R^1$ represents hydrogen or a lower alkyl group, $R_2$ represents hydrogen, a lower alkyl group, or

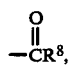

$R^3$ represents hydrogen, a lower alkyl group, or

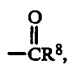

$R^4$ represents hydrogen or a lower alkyl group,
$R^5$ represents hydrogen or a lower alkyl group,
$R^6$ represents hydrogen, a lower alkyl, a substituted or unsubstituted aryl group, or —COOR$^{15}$,
$R^7$ represents hydrogen, halogen or lower alkyl,
$R^8$ represents a lower alkyl or a substituted or unsubstituted carbocyclic aryl group,
$R^{15}$ represents hydrogen or a lower alkyl, and n is 0 to 8, n being 0 when $R^6$ represents lower alkyl, are disclosed as an active therapeutic substances for the treatment of inflammatory conditions, allergic conditions and disorders related to loss of gastrointestinal integrity.

6 Claims, No Drawings

BENZIMIDAZOLES AS 5-LIPOXYGENASE INHIBITORS

This application is a continuation of application Ser. No. 766,275, filed Aug. 16, 1985, now abandoned.

The present invention relates to benzimidazoles, processes for their manufacture, pharmaceutical preparations containing them, and their use in the treatment of various disorders.

It is known that certain arachidonic acid metabolites may produce harmful effects in man. For example, products produced via lipoxygenation of the acid, for example the leukotrienes, are implicated in the pathology of arthritis and inflammation, as well as in the production and the pathology of asthma and other allergic diseases. Accordingly, a compound capable of selectively inhibiting 5-lipoxygenase while having weaker inhibiting effects on the cyclo-oxygenase enzyme is beneficial by preventing the formation of inflammatory and bronchoconstrictor mediators while having little inhibitory effect on protective prostaglandins in the stomach or on the bronchodilatory cyclo-oxygenase products, for example, prostacyclin.

Further, products of the lipoxygenase pathway may adversely affect the integrity of the gastro-intestinal mucosa. Inhibition of lipoxygenase activity may lead to stimulation of cytoprotective prostaglandin production, particularly prostacyclin and $PGE_2$. This inhibition may therefore be of use in maintaining or establishing the integrity of the gastro-intestinal mucosa.

We have now found that certain benzimidazoles inhibit the 5-lipoxygenase enzyme, and accordingly the present invention provides a benzimidazole containing an optionally etherified or esterified hydroxy group in the 4-position and a lipophilic group, the latter advantageously being in the 2-position.

The compounds of the invention find use in the treatment of inflammatory conditions, for example rheumatism and arthritis, in the treatment and prophylaxis of bronchial asthma, rhinitis, hay fever and allergic eczema, and in the treatment of disorders related to loss of gastro-intestinal integrity, for example peptic ulcers, mucosal erosions and erosive gastritis.

U.S. Pat. No. 2663712, DE-OS No. 1921911 and J.C.S., [1956] 569 disclose certain benzimidazoles; there is, however, in none of these documents any suggestion of the possibility that any of the compounds disclosed may have any pharmaceutical use. Certain of these compounds were disclosed in J. Pharm. and Pharmacol 1956, 8, 661-5 and reported to have no significant anti-bacterial activity.

More especially, the present invention provides a compound of the general formula I

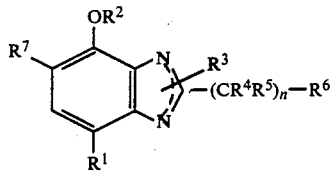

or a salt or solvate, e.g., hydrate, thereof, in which,
$R^1$ represents hydrogen or a lower alkyl group,
$R_2$ represents hydrogen, a lower alkyl group, or

$R^3$ represents hydrogen, a lower alkyl group, or

$R^4$ represents hydrogen or a lower alkyl group,
$R^5$ represents hydrogen or a lower alkyl group,
$R^6$ represents hydrogen, a lower alkyl, a substituted or unsubstituted aryl group, or $-COOR^{15}$,
$R^7$ represents hydrogen, halogen or lower alkyl,
$R^8$ represents a lower alkyl or a substituted or unsubstituted carbocyclic aryl group,
$R^{15}$ represents hydrogen or a lower alkyl, and n is 0 to 8, n being 0 when $R^6$ represents lower alkyl,
as an active therapeutic substance.

When used herein with reference to alkyl or alkoxy groups, the term "lower" means that the group contains up to 6 carbon atoms, preferably up to 4 carbon atoms. Alkyl radicals may have straight or branched chains, and may be, for example, methyl, ethyl, n-propyl, isopropyl, n-butyl, isobutyl or tert-butyl.

In formula I, the symbol

means that $R^3$ may be attached to either of the nitrogen atoms of the imidazole ring and that, when $R^3$ represents hydrogen, tautomerism exists; both tautomers are included within the scope of this invention. When $R^3$ does not represent hydrogen, the two compounds differ because of the asymmetry of the benzene ring substituents, and both compounds are included within the scope of this invention.

When $R^1$ represents a lower alkyl group, it is advantageously a methyl. It is preferred that both $R^2$ and $R^3$ represent hydrogen; when either of them represents lower alkyl, it is advantageously the methyl group and when either of them represents

it is advantageous that $R^8$ represents methyl. It is preferred that both $R^4$ and $R^5$ represent hydrogen; when either of them represents lower alkyl, methyl is advantageous.

When $R^4$ and $R^5$ are different, stereoisomerism may arise and it will be appreciated that the present invention provides all isomers individually and in admixture.

When $R^6$ or $R^8$ represents aryl, the group may be carbocyclic group, suitably

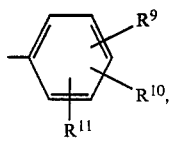

which is preferred, or

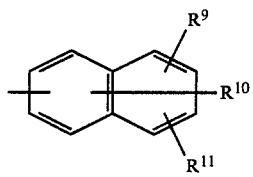

in which each $R^9$, $R^{10}$, $R^{11}$ independently represents hydrogen, hydroxy, lower alkoxy, e.g., methoxy, lower alkyl, e.g., methyl, or halogen, preferably chlorine or bromine, trifluoromethyl, nitrile, nitro, amino, $NR^{12}R^{13}$ (in which $R^{12}$ and $R^{13}$ are independently hydrogen or lower alkyl), -COOH, -COOR$^{14}$,

or

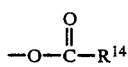

(in which $R^{14}$ is lower alkyl or aryl), or in which $R^9$ and $R^{10}$ are linked and together represent methylenedioxy or $C_3$–$C_4$ alkylene. In the case of a substituted naphthyl group the substitutuent, or each substituent independently if there are more than one, may be on either the linked ring or the non-linked ring.

Alternatively $R^6$ may represent a heterocyclic aryl group, suitably

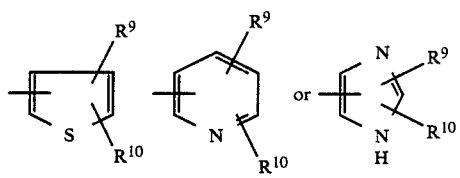

in which $R^9$ and $R^{10}$ have the meanings given above.

When $R^6$ represents imidazolyl or pyridyl, it advantageously represents 1-imidazolyl or 3- or 4-pyridyl.

When $R^6$ represents $COOR^{15}$, then advantageously $R^4$ and $R^5$ represent hydrogen.

When $R^7$ represents a halogen, chlorine is preferred; when it represents an alkyl group, tert-butyl is preferred.

Within the compounds of formula I are a preferred group of compounds of formula II

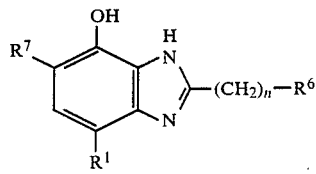

in which $R^1$ represents a lower alkyl, particularly methyl, group, $R^7$ represents hydrogen or a lower alkyl, particularly tert-butyl, group, $R^6$ represents an aryl group, particularly phenyl, mono, di or tri-substituted with methoxy or methyl, and n is 0 to 5, particularly 1.

The present invention further provides a compound of the general formula III

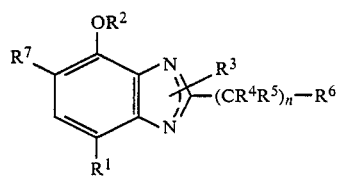

or a salt or solvate thereof, in which $R^1$, $R^2$, $R^3$, $R^4$, $R^5$, $R^6$, $R^7$, $R^8$ and $R^{15}$ are as defined for formula I, subject to the provisos that in a compound in which $R^2$ and $R^3$ represent hydrogen or lower alkyl, $R^6$ represents hydrogen, lower alkyl or carbocyclic aryl, $R^7$ represents H or alkyl and n=0, $R^1$ does not represent hydrogen, and that in a compound in which $R^1$, $R^2$, $R^6$ and $R^7$ represent hydrogen or methyl and n=0, $R^3$ does not represent hydrogen or an alkyl group having up to 4 carbon atoms.

Preferred substituents within the above-mentioned substituents are as indicated with reference to formula I and formula II. It will be appreciated that when $R^3$ represents hydrogen tautomerism exists corresponding to that existing in Formula I.

The present invention also provides a physiologically tolerable compound of the general formula I, or a physiologically tolerable salt or solvate thereof, for use in treatment of the human or animal body.

The present invention also provides a pharmaceutical preparation comprising a physiologically tolerable compound of the general formula I, or a physiologically tolerable salt or solvate thereof, in admixture or conjunction with a pharmaceutically acceptable carrier.

Preferably, a pharmaceutical preparation of the invention is in unit dosage form and in a form adapted for use in the medical or veterinarial fields. For example, such preparations may be in a pack form accompanied by written or printed instructions for use as an agent in the treatment on prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or preparation of the invention may be formulated for administration by any route, the preferred route depending upon the disorder for which treatment is required, and is preferably in unit dosage form or in a form that a human patient may administer to himself in a single dosage. Advantageously, the preparation is suitable for oral, rectal, topical, parenteral-intravenous or intramuscular administration or through the respiratory tract. Preparations may be designed to give slow release of the active ingredient.

Preparations may, for example, be in the form of tablets, capsules, sachets, vials, powders, granules, lozenges, reconstitutable powders, or liquid preparations, for example solutions or suspensions, or suppositories. Preparations which are especially suitable for administration to the respiratory tract and for topical administration are discussed in more detail below.

The preparations, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid preparations may be obtained by conventional methods of blending, filling tabletting or the like. Repeated blending operations may be used to distribute the active agent throughout those preparations employing large quantities of fillers. When the preparation is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharamaceutical practice, in particular with an enteric coating.

Preparations for oral administration as liquids may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, propylene glycol or ethyl alcohol, glycerine, water or normal saline; preservatives, for example methyl or propyl p-hydroxybenzoate or sorbic acid; and if desired conventional flavouring or colouring agents.

For parenteral administration, fluid forms are prepared utilizing the compound and a sterile vehicle, and, depending on the concentration used, may be either suspended or dissolved in the vehicle. In preparing solutions the compound may be dissolved in water for injection and filter sterilized before filling into a suitable vial ampoule and sealing. Advantageously, adjuvants, for example a local anaesthetic, a preservative and buffering agents can be dissolved in the vehicle. To enhance the stability, the compositions can be frozen after filling into the vial and the water removed under vacuum. Parenteral suspensions are prepared in substantially the same manner, except that the compound is suspended in the vehicle instead of being dissolved, and sterilization is not accomplished by filtration. The compound may be sterilized by exposure to ethylene oxide before suspending in the sterile vehicle. Advantageously, a surfactant or wetting agent is included in the composition to facilitate uniform distribution of the compound.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For topical administration, the preparations may also be presented as an ointment, cream, lotion, gel, aerosol, or skin paint for topical application.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

For use in treatment of inflammatory diseases, a preparation of the invention will preferably be in a form suitable for oral administration, for example a tablet or capsule or a sachet containing reconstitutable powder. A unit dose will generally contain from 20 to 1000 mg and preferably will contain from 30 to 500 mg, in particular 50, 100, 150, 200, 250, 300, 350, 400, 450, or 500 mg. The preparation may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

For treatment of disorders related to the loss of gastro-intestinal integrity, a unit dose will normally contain 1 to 2000 mg, for example 5 to 1000 mg, of the active ingredient. Unit doses will normally be administered at least once a day, for example 1, 2, 3, 4, 5 or 6 times a day such that the total daily dose is normally in the range 0.1 to 30 mg/kg body weight per day, e/g. 7 to 2000 mg/day for a 70 kg human adult.

For treatment of all the above-mentioned disorders, the compositions may contain from 0.1% by weight to 99% by weight, preferably from 10 to 60% by weight, of the active ingredient, depending on the method of administration.

The present invention also provides a method of treatment which comprises administering a physiologically tolerable compound of the formula I or a physiologically tolerable salt thereof to a human or animal body.

The present invention also provides a process for the manufacture of a compound of the formula I, or formula III, wherein a compound of the formula IV

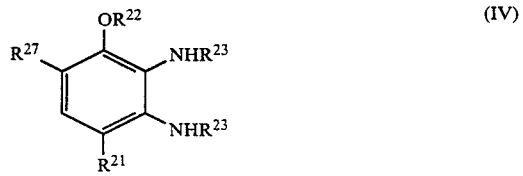

(IV)

wherein $R^{21}$ represents hydrogen or a lower alkyl group, or a group or atom convertible thereto, $R^{22}$ represents hydrogen or a lower alkyl group, or a group or atom convertible thereto, one $R^{23}$ represents hydrogen and the other $R^{23}$ represents hydrogen or a lower alkyl group, or a group or atom convertible thereto, and wherein $R^{27}$ represents hydrogen, halogen, or alkyl, or a group or atom convertible thereto, is reacted with a compound of formula V.

wherein $R^{26}$ represents —$(CR^4R^5)_n$-$R^6$, or a group convertible thereto, wherein $R^4$, $R^5$, and $R^6$, and n each have the meanings given above with reference to formula I or formula III and $R^{28}$ represents a leaving group or hydrogen to form a compound of the formula VI:

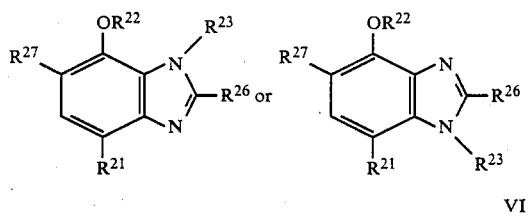

and, if required, a nitrogen atom of, and/or the 4-oxygen atom on, the benzimidazole nucleus is acylated with a group of the formula

or is alkylated, and if required protecting groups are removed, to form a compound of the formula I or formula III, and if required forming a salt or solvate thereof.

Preferably any such salt or solvate is pharmaceutically acceptable. However salts or solvates which are not pharmaceutically acceptable may be useful as intermediates in the production of pharmaceutically acceptable salts or the compounds per se.

The present invention also provides a process for the manufacture of a compound of the formula I or formula III wherein the compound of formula IV is obtained by reducing a compound of the formula VII

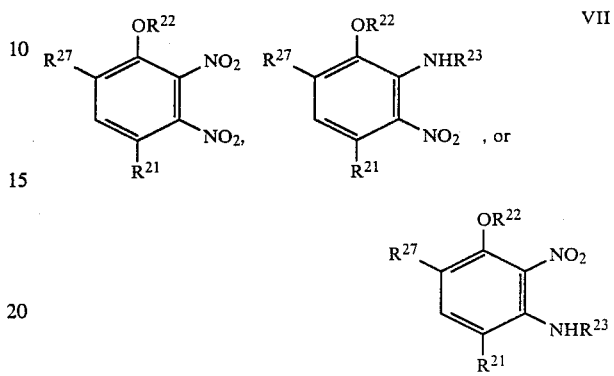

wherein $R^{21}$, $R^{22}$ and $R^{23}$ and $R^{27}$ have the meanings given above in relation to formula IV, and if desired or required protective groups are removed to form the compound of the formula IV.

Compounds of the Formula VII in which an $R^{23}$ group represents alkyl may be made, in the case of such an $R^{23}$ group meta to the $OR^{22}$ group, for example by nitration in the meta position, reduction of the nitro group, monoalkylating the amino group, and nitrating in the ortho position.

The compounds in which the alkyl $R^{23}$ group is ortho to the $OR^{22}$ group may be made, for example, by treating the ortho, meta dinitro compound with an amine of the formula $R^{23}NH_2$, which preferentially replaces the ortho nitro group.

Reduction of a compound of the formula VII may be effected by conventional chemical methods or preferably by catalytic methods. Catalytic reduction, using for example palladium on charcoal or Raney nickel, is conveniently effected in a conventional hydrogenation solvent, such as a lower alkanol, e.g., ethanol. When $R^{22}$ represents hydrogen, it may be protected by a benzyl group, introduced by, for example, heating with a benzyl halide/$K_2CO_3$/KI or NaI system in acetone or by a methyl group, introduced by $CH_3I/K_2CO_3$ in acetone.

Reaction of a compound of the formula IV, whether resulting from manufacture by reduction of a compound of the formula VII and, if desired or required, removal of protecting groups, or otherwise obtained, within a compound of the formula V, is preferably effected by heating with a compound of the formula V

wherein $R^{28}$ represents a leaving group. For example the compound may be an acid, acid chloride, acid anhydride, including a mixed anhydride of the acid $R^{26}COOH$ and haloformate ester. The presence of an acid catalyst, e.g., HCl, may be necessary.

A compound of the formula VIII

R²⁶CHO    (VIII)

may react with the compounds of the formula IV under the conditions in Arz. Forsch., 1967, 17, 55 when R²⁶ is an aryl group. Further generally applicable methods of benzimadazole synthesis are described in Chem Revs, 1974, 74(3), 279.

Removal of protecting groups if desired or required may be effected by methods known per se, for example heating with HBr or aqueous hydrochloric acid to remove a methyl protecting group or catalytic hydrogenation to remove the benzyl group, using, for example, palladium/charcoal as catalyst.

The invention further provides a process in which one compound of the formula I is converted to another compound of the formula I.

The present invention in particular provides a process for preparing a compound of the formula I in which $R_3$ represents

which comprises treating a compound of the formula I in which $R^3$ represents H with an appropriate acylating agent. If $R^2$ represents hydrogen, it is desirably protected, as by a benzyl group, during the reaction. Advantageously, the reaction employs the appropriate acyl halide, preferably the chloride, and is carried out in basic conditions using, for example, triethylamine and chloroform as the medium.

The present invention further provides a process for the manufacture of an ester of a compound of the formula I, which comprises acylating a compound of the formula I in which $R_2$ represents hydrogen, under conditions preventing or inhibiting acylation of the N-atoms of the benzimidazole nucleus, for example in a trifluoracetic acid medium, other reactive groups in the molecule being blocked by a protective group where necessary. The acylation preferably attaches a group of the formula

to the oxygen atom at the 2-position.

Compounds of the formula I in which $R^7$ is other than hydrogen may be made by methods known per se. For example, a compound in which $R^7$ represents halogen, e.g., bromine or chlorine, may be prepared by halogenating phenol, if desired p-substituted as by alkyl, in the 2-position followed by sequential nitration in the 5 and 6 positions, the phenolic hydrogen being protected at the required stages. A similar procedure may be used when $R^7$ represents an alkyl group; subsequent reduction to the diamino precursor of formula IV and its conversion to the benzimidazole of formula I may be effected as described above.

Reaction schemes for the preparation of 5-substituted benzimidazoles and of compounds of the formula VII in which one $R^{23}$ does not represent hydrogen are given below by way of illustration only. $R^1$, $R^{21}$, $R^{27}$ and $R^{26}$ have the meanings given above in relation to formula I (or formula III) IV, V and VI respectively, $R^1$ preferably being methyl. Certain of the intermediates are novel, and the present invention also provides these compounds, and the process for their manufacture herein described.

In particular the present invention provides novel intermediates of the formula IX:

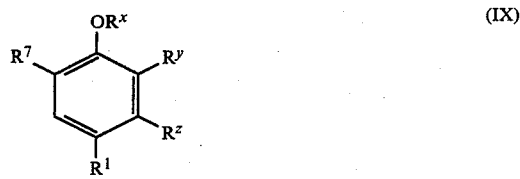

in which $R^1$ is as defined for formula I, $R^x$ is benzyl or mesyl or $R^2$ as defined for formula I, $R^y$ is hydrogen, $NO_2$ or $NH_2$, and $R^z$ is $NO_2$ or $NH_2$, and $R^7$ is tert. butyl.

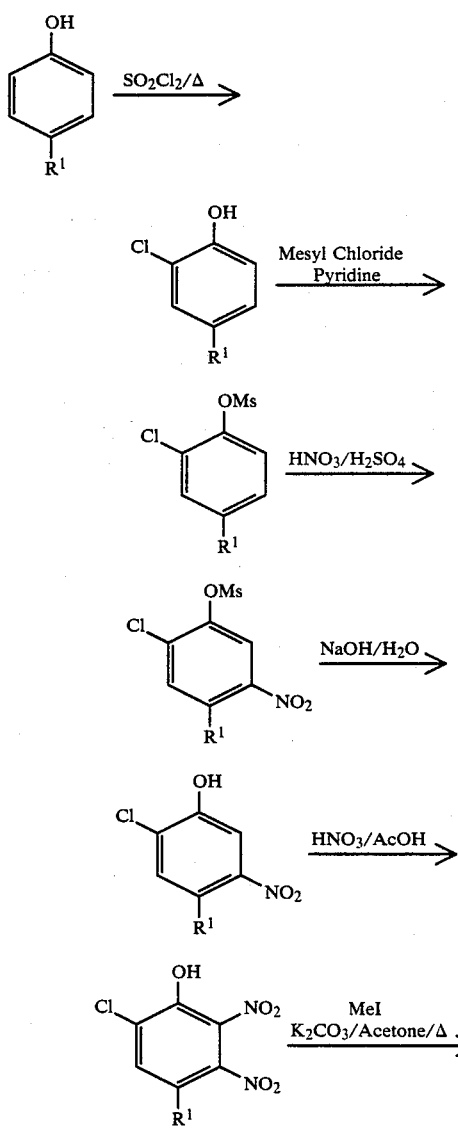

-continued
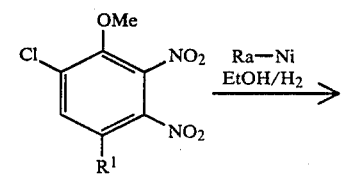
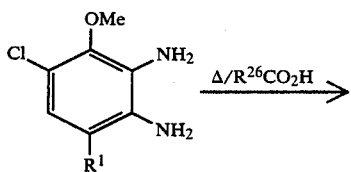
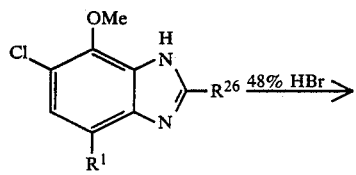
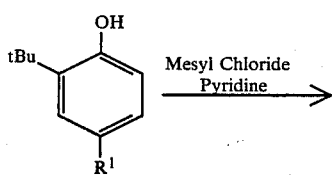
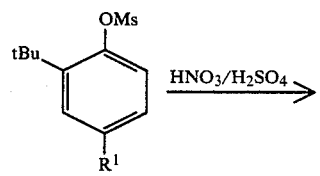
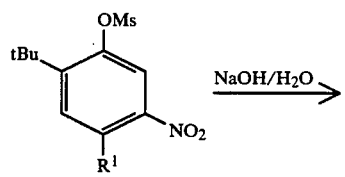
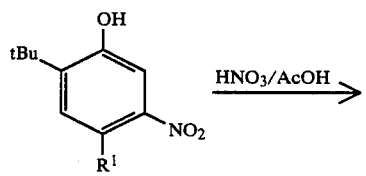
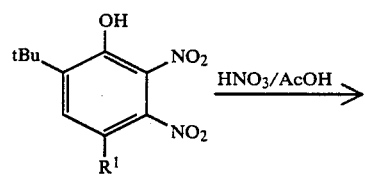
-continued
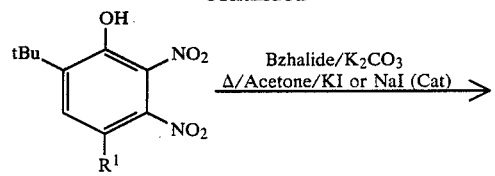
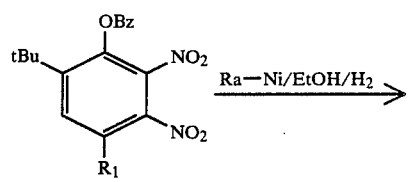
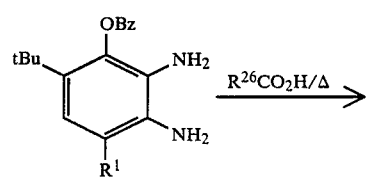
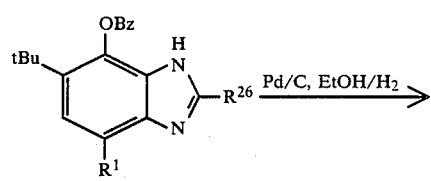
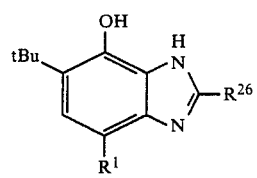
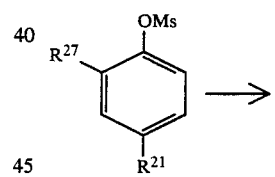
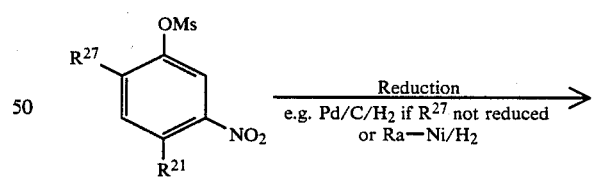
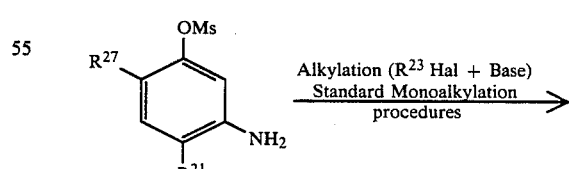
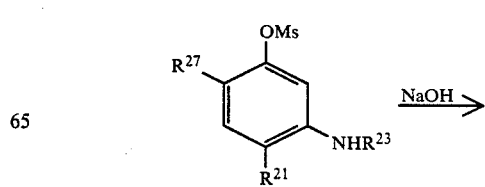

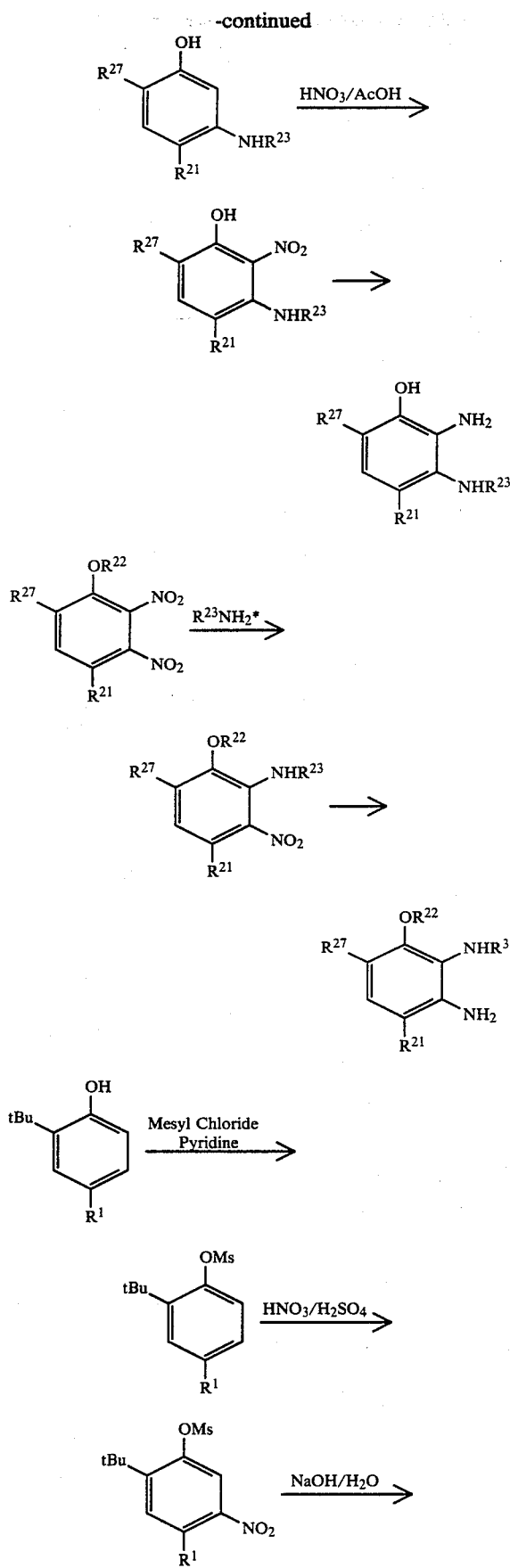

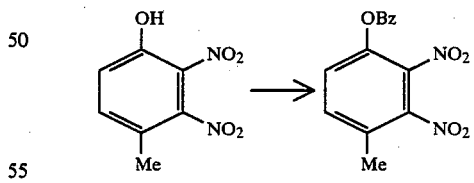

*see J.F. Bunnett and R.E. Zahler, Chem. Rev. 1951, 49, 354
R.E. Markwell, Chem. Commun. 1979, 428

The present invention also provides a process for the manufacture of a pharmaceutical preparation of a compound of the formula I, which comprises preparing a physiologically tolerable compound of the formula I, advantageously by the reaction of a compound of the formula IV with a compound of the formula V, the compound of the formula IV preferably having been made by reduction of the nitro groups in a compound of the formula VII to amine groups, and if required removing protecting groups, and if required forming a physiologically tolerable salt thereof, and admixing the physiologically tolerable compound or salt with a pharmaceutically acceptable excipient.

The following descriptions illustrate the preparation of intermediates for the compounds of the invention. The following examples illustrate the invention:

DESCRIPTION 1

4-Benzyloxy-2,3-dinitrotoluene

A mixture of 4-methyl-2,3-dinitrophenol[1] (12.0 g), anhydrous potassium carbonate (15 g), potassium iodide (0.1 g), benzyl chloride (25 g) in acetone (A.R., 150 ml) was heated and stirred under reflux for 18 hr.

The mixture was cooled, filtered, and the filtrate evaporated to dryness in vacuo. The residue was taken up in chloroform (400 ml) and washed with water, dried (Na$_2$SO$_4$), filtered and evaporated to half volume in vacuo. Addition of pentane (150 ml) gave the title compound, 16.2 g, (93%) m.p. 116°–118° C.

M. F. Dadswell and J. Kenner, J. Chem. Soc. 580 (1927).

DESCRIPTION 2

2,3-Diamino-4-benzyloxytoluene

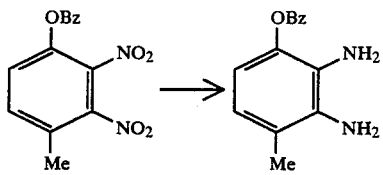

4-Benzyloxy-2,3-dinitrotoluene (7 g), in ethanol and Raney-nickel (3 g), was hydrogenated at room temperature and pressure until uptake of hydrogen ceased (3 h). The colourless solution was filtered (celite) and evaporated to dryness in vacuo to afford the title compound as an unstable oil, (5 g), which was used immediately for the next step.

DESCRIPTION 3

2-Benzyl-4-benzyloxy-7-methylbenzimidazole

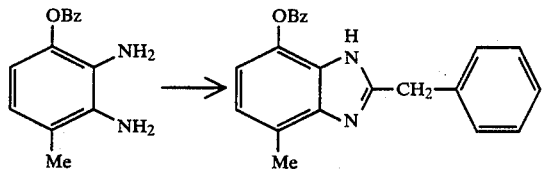

A mixture of 2,3-diamino-4-benzyloxytoluene (5 g) and phenylacetic acid (23 g) was heated at 120° C. for 1 h. The mixture was cooled, dissolved in chloroform and washed with 10% sodium carbonate solution, and then with water, dried (Na$_2$SO$_4$), and evaporated to dryness in vacuo. The residue was recrystallized from ethyl acetate-hexane to afford the title compound, (4.4 g), m.p. 198°-200° C.

Anal: C$_{22}$H$_{20}$N$_2$O requires C,80.45; H,6.15; N,8.55%.
Found: C, 80.35; H, 6.05; N,8.45%.
Similarly prepared was:

DESCRIPTION 4

2-Phenethyl-4-benzyloxy-7-methylbenzimidazole

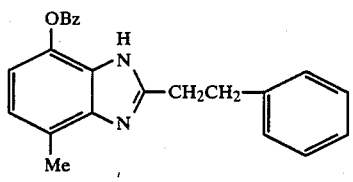

m.p. 203°-4° C. (Ethanol).

DESCRIPTION 5

4-Benzyloxy-7-methyl-2-phenylbenzimidazole

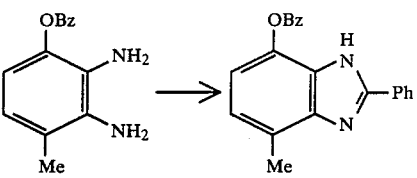

A mixture of 2,3-diamino-4-benzyloxytoluene (5.0 g) and benzaldehyde (5.52 g, 2 mol. equiv.) in xylene (75 ml) was heated under reflux for 3 h, and then left for 18 h at room temperature. The resulting crystalline product was filtered, washed with ether, and recrystallized from ethanol to afford the title compound, 4.13 g, m.p. 221°-224° C.

Anal: C$_{21}$H$_{18}$N$_2$O requires C,80.25; H,5.75; N,8.9%
Found: C,80.15; J,5.60; N,8.8%
Similarly prepared was

DESCRIPTION 6

2-n-Propyl-4-benzyloxy-7-methylbenzimidazole

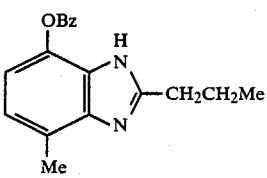

m.p. 192°-194° C. (ethanol-ethyl acetate).
Anal: C$_{18}$H$_{20}$N$_2$O requires C,77.11; H,7.19; N,9.99%.
Found: C,76.85; H,7.19; N,9.91%.

DESCRIPTION 7

2-(4'-Methoxybenzyl)-4-benzyloxy-7-methylbenzimidazole

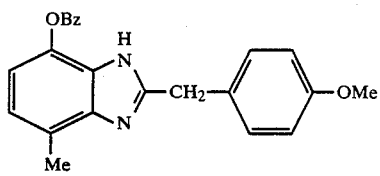

m.p. 181°-183° C. (ethyl acetate).
Anal: C$_{23}$H$_{22}$N$_2$O$_2$ requires C,77.07; H,6.19; N,7.82%.
Found: C,77.22; H,6.26; N,7.81%.

DESCRIPTION 8

2-Nitro-4-hydroxy-5-tert-butyltoluene-O-mesylate

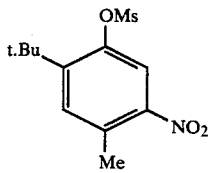

Mesyl chloride (147 g) was added dropwise over 0.5 h to a solution of 3-tert-butyl-4-hydroxytoluene (200 g) in pyridine (500 ml) at 0° C. The solution was stirred at 10° C. for 1 h and then at room temperature for a further 3 h. It was poured into excess 5N-hydrochloric acid and extracted with dichloromethane. The organic layer was washed with 5N-hydrochloric acid, water and dried (Na₂SO₄). Evaporation to dryness in vacuo afforded crude 3-tert-butyl-4-hydroxytoluene-O-mesylate (250 g) which was dissolved in concentrated sulphuric acid (750 ml) and cooled to 0° C. A mixture of concentrated nitric acid (93 g) and concentrated sulphuric acid (175 ml) was added dropwise over 1 h maintaining the temperature at 0° C. The solution was poured onto ice, and the resulting solid was collected, washed with water and air-dried to afford the title compound (260 g), m.p. 69°–78° C. sufficiently pure for the next step. A portion was recrystallised from chloroformpentane, m.p. 91°–92° C.

Anal: $C_{12}H_{17}NO_5S$ requires C,50.16; H,5.96; N,4.87%.

Found: 49.98; H,5.98; N,4.85%.

DESCRIPTION 9

2-Nitro-4-hydroxy-5-tert-butyltoluene

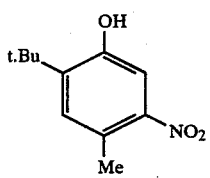

The crude product from Description 8 (260 g) was stirred with a solution of sodium hydroxide (130 g) in water (800 ml) at 60°–70° C. until all the solid had dissolved (1.5 h). The solution was filtered and poured onto an excess of ice and 5N hydrochloric acid. The mixture was extracted with dichloromethane and the organic layer was washed with water and dried (Na₂SO₄). Evaporation to dryness in vacuo afforded the title compound (140 g) sufficiently pure for the next step.

A portion was recrystallised from dichloromethane-pentane, m.p. 96°–98° C.

Anal: $C_{11}H_{15}NO_3$ requires C,63.4; H,7.23; N,6.69%.

Found: C,63.22; H,7.2; N,6.69%.

DESCRIPTION 10

2,3-Dinitro-4-hydroxy-5-tert-butyltoluene

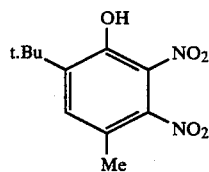

A solution of fuming nitric acid (10.02 ml) in acetic acid (15 ml) was added dropwise over 15 min to a solution of the crude product from Description 9 (35 g) in acetic acid (60 ml) while maintaining the temperature at 18°–20° C. After a further 10 min the solution was poured onto ice and the resulting solid was collected and washed with water. It was dissolved in dichloromethane, washed with water and dried (Na₂SO₄). The product was purified by column chromatography on Silica Gel 60 (250 g) eluting with dichloromethane. Recrystallisation from dichloromethane-pentane afforded the title compound (25 g), m.p. 104°–105° C.

Anal: $C_{11}H_{14}N_2O_5$ requires C,51.97; H,5.55; N,11.02%.

Found: C,51.88; H,5.62; N,11.00%.

DESCRIPTION 11

2,3-Diamino-4-hydroxy-5-tert-butyltoluene

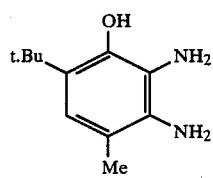

A solution of 2,3-dinitro-4-hydroxy-5-tert-butyltoluene (Description 10) (7.5 g) in ethanol (350 ml) was hydrogenated at room temperature and atmospheric pressure over 10% palladium-carbon (2.5 g) until uptake of hydrogen ceased. The solution was filtered under nitrogen and evaporated to dryness in vacuo to afford the unstable title compound, m.p. 129°–136° C., which was used immediately for the next reaction.

DESCRIPTION 12

O-Benzyl-2,3-dinitrophenol

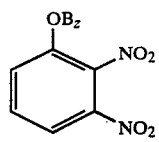

A mixture of 2,3-dinitrophenol[1] (10.0 g), anhydrous potassium carbonate (11.0 g) and benzyl chloride (8.22 g) in acetone (250 ml) was heated under reflux for 8 h. The solution was filtered and the filtrate evaporated to dryness in vacuo.

The residue was re-crystallised from chloroform-hexane to afford the title compound (14.2 g), m.p. 100°–101° C.

Reference

[1] A. Bantlin, Berichte, 11, 2104, (1878).

EXAMPLE 1

2-Benzyl-4-hydroxy-7-methylbenzimidazole

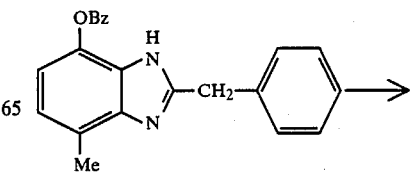

-continued

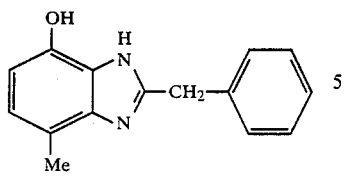

A solution of 2-benzyl-4-benzyloxy-7-methylbenzimidazole (3.0 g) in ethanol (400 ml) and 10% palladium-carbon (1.5 g) was hydrogenated at room temperature and pressure until uptake of hydrogen ceased. The mixture was filtered (celite), and the filtrate was evaporated to dryness in vacuo and recrystallized from ethanol-ether to afford the title compound (1.85 g), m.p. 204°–205° C.

Anal: $C_{15}H_{14}N_2O$ requires C,75.6; H,5.9; N, 11.75%. Found: C,75.35; H,5.85; N,11.7%.

| $\delta[(CD_3)_2SO]$ | 2.4 (3H,s) |
|---|---|
| | 4.2 (2H,s) |
| | 6.45 (1H,d,J=8Hz) |
| | 6.75 (1H,d,J=8Hz) |
| | 7.3 (5H,m) |
| | 9.6 (1H,br,s) |

EXAMPLE 2

2-(4-Chlorobenzyl)-4-methoxy-7-methylbenzimidazole

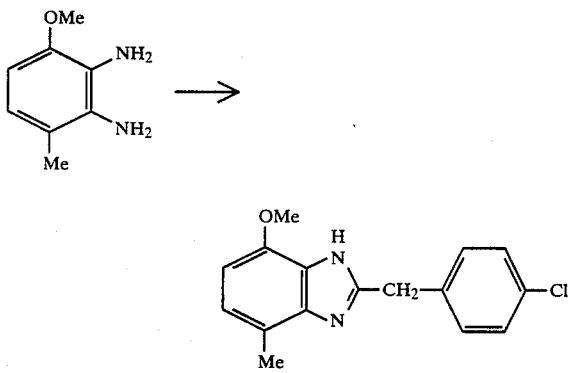

A mixture of 2,3-diamino-4-methoxytoluene [prepared by hydrogenation of 4-methoxy-2,3-dinitrotoluene (7.5 g) over 10% palladium-carbon (2.5 g) in ethanol] and 4-chlorophenylacetic acid (23 g) was heated at 130°–150° C. for 4.5 h under nitrogen. The mixture was cooled, dissolved in chloroform, washed with 10% sodium carbonate solution, then with water, dried (Na₂SO₄) and evaporated to dryness in vacuo. The product was recrystallized from chloroform-pentane to afford the title compound, (5.75 g), m.p. 195°–197° C.

Anal: $C_{16}H_{15}ON_2Cl$ requires C,67.00; H,5.25; N,9.75; Cl,12.35%

Found: C,67.05; H,5.30; N,9.85; Cl,12.60%

EXAMPLE 3

2-(4-Chlorobenzyl)-4-hydroxy-7-methylbenzimidazole hydrobromide

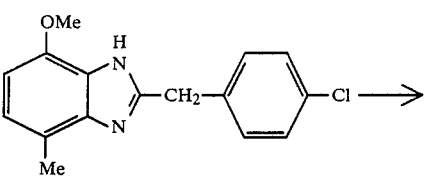

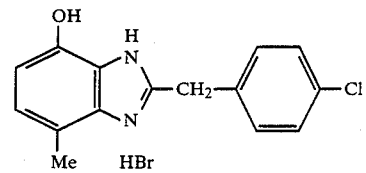

A suspension of 2-(4-chlorobenzyl)-4-methoxy-7-methylbenzimidazole (4.0 g) in 48% aqueous hydrobromic acid (400 ml) under nitrogen was heated at 130° for 5 h, then evaporated to dryness in vacuo. The residue was recrystallized from ethanol-ether to afford the title compound (3.95 g), m.p. 275°–277° C.

Anal: $C_{15}H_{30}ON_2Cl.HBr$. requires C,50.95; H,4.0; N,7.9%

Found: C,50.60; H,3.9; N,7.8%

After preparing the free base in a manner similar to that described in Example 1, the following were prepared by the addition of ethereal hydrogen chloride to a solution of the free base in ethanol-ether.

EXAMPLE 4

2-Phenethyl-4-hydroxy-7-methylbenzimidazole hydrochloride

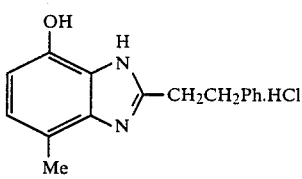

m.p. 238°–40° C.

Anal: $C_{16}H_{16}N_2OHCl$ requires C,66.55; H,5.93; N,9.70%;

Found: C,66.71; H,5.96; N,9.67%

EXAMPLE 5

2-Phenyl-4-hydroxy-7-methylbenzimidazole hydrochloride

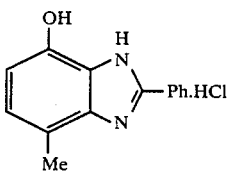

m.p. 252°–6° C. (dec).

Anal: $C_{14}H_{12}ON_2HCl$ requires C,64.5; H,5.00; N,10.75; Cl,13.60%

Found: C,64.2; H,4.85; N,10.55; Cl.13.55%
Prepared in an analogous manner were:

EXAMPLE 6

2-(Pyrid-3-yl)methyl-4-hydroxy-7-methylbenzimidazole

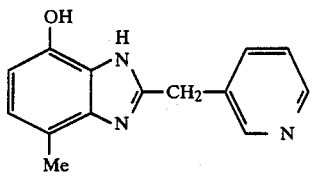

m.p. 264°–268° C. (methanol/ethylacetate/ether)
Anal: $C_{14}H_{13}N_3O$ requires C,70.28; H,5.48; N,17.56%.
Found: C,70.15; H,5.62; N,17.23%.

EXAMPLE 7

2-(Naphth-2-ylmethyl)-4-hydroxy-7-methylbenzimidazole hydrochloride

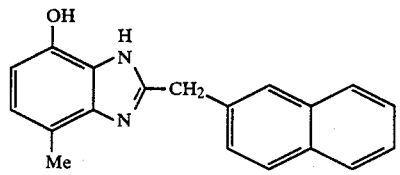

m.p. >230° C. (dec)
Anal: $C_{19}H_{16}N_2O.HCl$ requires C,70.25; H,5.28; N,8.63; Cl,10.92%.
Found: C,70.41; H,5.31; N,8.59; Cl,11.04%.

EXAMPLE 8

2-Benzyl-4-hydroxy-5-tert-butyl-7-methylbenzimidazole

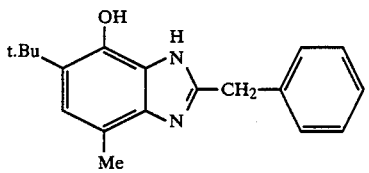

A mixture of 2,3-diamino-4-hydroxy-5-tert-butyltoluene (Description 11) (prepared from 12 g of 2,3-dinitro-4-hydroxy-5-tert-butyltoluene) and phenylacetic acid (30 g) was heated for 1 h at 120°–130° C. under nitrogen. The reaction product was extracted with chloroform, washed with 10% sodium carbonate, water, and dried ($Na_2SO_4$). The chloroform solution was evaporated to dryness in vacuo, and recrystallised from chloroformethylacetate-pentane to afford the title compound (9.3 g), m.p. 226°–228° C.
Anal: $C_{19}H_{22}N_2O$ requires C,77.52; H,7.53; N,9.52%.
Found: C,77.31; H,7.64; N,9.76%.

EXAMPLES (9a) AND (9b)

5-tert-Butyl-4-hydroxy-2-(4′-methoxybenzyl)-7-methylbenzimidazole (9a) and the hydrochloride salt (9b)

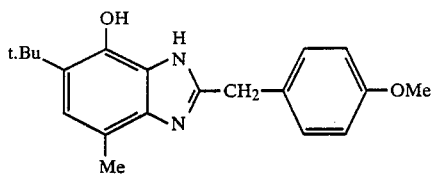

Example 9a Free Base
Example 9b HCl

The title compound (9a) was prepared in an analogous manner to Example 8. m.p. 269°–270° C. (ethanol/ether)
The free base (9a) was treated with ethanolic-hydrogen chloride to afford the hydrochloride salt (Example 9b). m.p. 232°–235° C. (ethanol/ether).
Anal: $C_{20}H_{24}N_2O_2$ HCl requires C,66.56; H,6.98; N,7.76; Cl,9.82%.
Found: C,66.58; H,7.06; N,7.79; Cl,10.00%.

EXAMPLE 10

2-(4′-Methylbenzyl)-4-hydroxy-7-methylbenzimidazole

This compound was prepared in a analogous manner to Example 1.

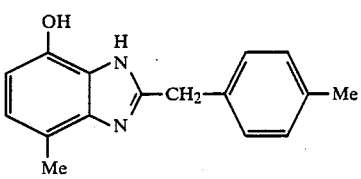

m.p. 217°–8° C.
Anal: $C_{16}H_{16}N_2O$ requires C,75.86; H,6.30; N,11.04%.
Found: C,75.25; H,6.37; N,11.06%.
The following were prepared in an analogous manner to Example 4.

EXAMPLE 11

2-n-Propyl-4-hydroxy-7-methylbenzimidazole hydrochloride

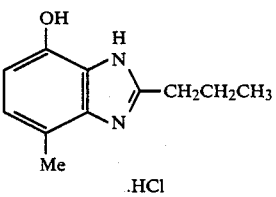

m.p. 204°–206° C. (ethanol/ethyl acetate/ether)
Anal: $C_{11}H_{14}N_2O.HCl$ requires C,58.27; H,6.66; N,12.35; Cl,15.63%.
Found: C,58.25; H,6.97; N,12.30; Cl,15.79%.

EXAMPLE 12

2-(4'-Methoxybenzyl)-4-hydroxy-7-methylbenzimidazole hydrochloride

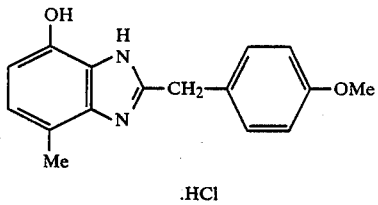

m.p. 228°–229° C. (ethanol-water)

Anal: $C_{16}H_{16}N_2O_2 \cdot HCl$ requires C,63.05; H,5.62; N,9.19; Cl,11.63%.

Found: C,62.95; H,5.88; N,9.08; Cl,11.68%.

EXAMPLE 13

"2-(3'-trifluoromethylphenyl)-4-hydroxy-7-methylbenzimidazole hydrochloride" (and) [the following chemical structure:]

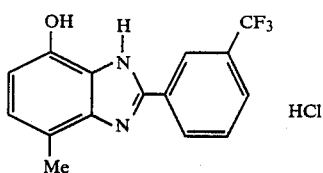

m.p. >280° C. (dec)

Anal: $C_{15}H_{11}F_3N_2O \cdot HCl$ requires C,54.80; H,3.68; N,8.52; Cl, 10.79%.

Found: C,54.58; H,3.62; N,8.45; Cl,10.50%.

EXAMPLE 14

"2-(4'-N,N-dimethylaminophenyl)-4-hydroxy-7-methylbenzimidazole hydrochloride" [and the following chemical structure:]

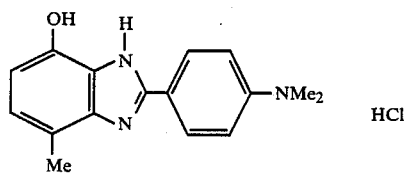

m.p. 175°–194° C.

Anal: $C_{16}H_{17}N_3O \cdot HCl$ requires C,63.26; H,5.97; N,13.81; Cl,11.67%.

Found: C,63.25; H,5.99; N,13.40; Cl,11.6%.

EXAMPLE 15

2-(Naphth-1-ylmethyl)-4-hydroxy-7-methylbenzimidazole hydrochloride

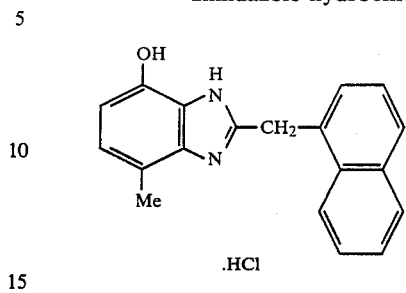

m.p. 262°–3° C.

Anal: $C_{19}H_{16}N_2O \cdot HCl$ requires C,70.26; H,5.28; N,8.63; Cl,10.92%.

Found: C,70.36; H,5.32; N,8.57; Cl,11.49%.

EXAMPLE 16

2-Benzyl-4-hydroxybenzimidazole

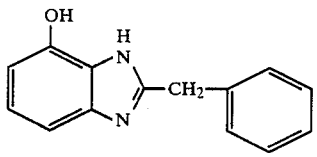

A solution of O-benzyl-2,3-dinitrophenol (Description 12) (4.5 g) in ethanol (300 ml) was hydrogenated at atmospheric pressure over Raney nickel (2 g) until uptake of hydrogen ceased. The solution was filtered and evaporated to dryness in vacuo to afford unstable O-benzyl-2,3-diaminophenol which was immediately heated with phenylacetic acid (20 g) at 140°–150° C. for 3 h. The product was heated under reflux with 5N-hydrochloric acid (70 ml) for 3 h and neutralised with 10% sodium carbonate. The mixture was extracted with chloroform, and the organic layer washed with 10% sodium carbonate, water and dried ($Na_2SO_4$). The recovered product was chromatographed on Silica Gel 60 (250 g) eluting with ethylacetate-chloroform (1:19) to afford the title compound (1.6 g), m.p. 172°–174° C. (ethanol/ether).

Anal: $C_{14}H_{12}N_2O$ requires C,74.98; H,5.39; N,12.49%.

Found: C,75.39; H,5.36; N,12.6%.

Similarly prepared was

EXAMPLE 17

2-(4'-Methoxybenzyl)-4-hydroxybenzimidazole hydrochloride

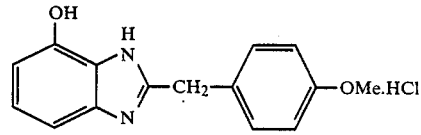

m.p. 194°–196° C. (methanol/ether)

Anal: $C_{15}H_{14}N_2O_2HCl$ requires C,61.75; H,5.52; N,9.60%.

Found: C,61.91; H,5.25; N,9.58%.

EXAMPLE 18

6-(4-Hydroxy-7-methyl-benzimidazol-2-yl)-hexanoic acid hydrochloride hydrate (3:3:1)

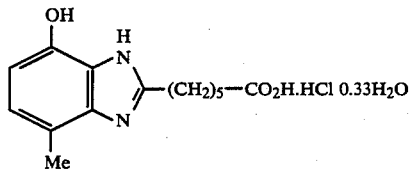

EXAMPLE 19

Ethyl 6-(4-hydroxy-7-methyl-benzimidazol-2-yl)-hexanoate hydrochloride

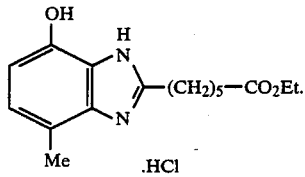

The compound of Example 18 (1.95 g) was heated under reflux in dry ethanol (100 ml) containing 5 drops conc. hydrochloric acid, for 0.5 h under nitrogen, and then evaporated to dryness in vacuo. The product was recrystallised from ethanol/ether to afford the title compound (1.99 g), m.p. 144°–146° C.

Anal: $C_{16}H_{22}N_2O_3.HCl$ requires C,58.8; H,7.09; N,8.57; Cl,10.84%.

Found: C,58.59; H,7.00; N,8.3; Cl,10.97%.

Similarly prepared were

EXAMPLE 20

Ethyl 5-(4-hydroxy-7-methyl-benzimidazol-2yl)pentanoate

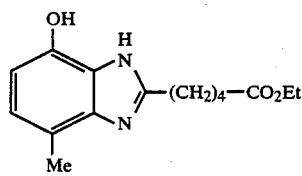

m.p. 133°–135° C. (ether)

Anal: $C_{15}H_{20}N_2O_3$ requires C,65.20; H,7.30; N,10.15%.

Found: C,64.95; H,7.13; N,9.96%.

EXAMPLE 21

5-(4-Hydroxy-7-methyl-benzimidazol-2yl)-pentanoic acid hydrochloride hemihydrate

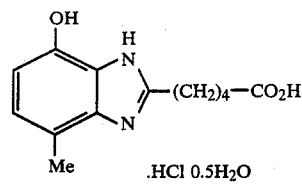

m.p. 186°–191° C. (water)

Anal: $C_{13}H_{16}N_2O_3.HCl.0.5H_2O$ requires C,53.13; H,6.17; N,9.53%.

Found: C,53.56; H,5.79; N,9.46%.

The following were prepared in an analogous manner to Example 4.

EXAMPLE 22

2-(2'-Furyl)-4-hydroxy-7-methylbenzimidazole hydrochloride: Ethanol (2:1)

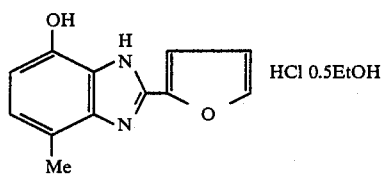

m.p. 256°–8° C. (dec). (ethanol-ether)

Anal. $C_{12}H_{10}N_2O_2.HCl: 0.5C_2H_6O$ requires C,56.29; H,5.12; N,10.10; Cl,14.06%. Found C,55.95; H,4.90; N,9.91; Cl,13.83%.

EXAMPLE 23

2-(Thien-2-ylmethyl)-4-hydroxy-7-methylbenzimidazole hydrochloride

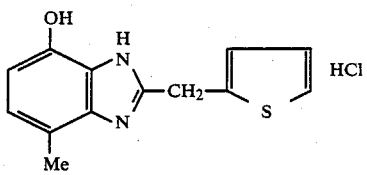

m.p. 206°–8° C. (ethanol-ether)

Anal. $C_{13}H_{12}N_2OS.HCl$ requires C,55.61; H,4.67; N,9.98; S,11.42; Cl,12.63%. Found C,56.22; H,4.77; N,9.72; S,11.03; Cl,12.63%.

EXAMPLE 24

2-(4'-Ethoxybenzyl)-4-hydroxy-7-methylbenzimidazole hydrochloride

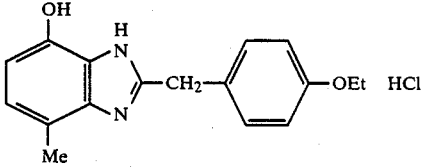

m.p. 227°–9° C. (ethanol-ether)

Anal. $C_{17}H_{18}N_2O_2 \cdot HCl$ requires C,64.05; H,6.01; N,8.79; Cl,11.12%. Found: C,63.98; H,5.96; N,8.62; Cl,10.91%.

EXAMPLE 25

2-(3',4',5'-Trimethoxybenzyl)-4-hydroxy-7-methylbenzimidazole hydrochloride

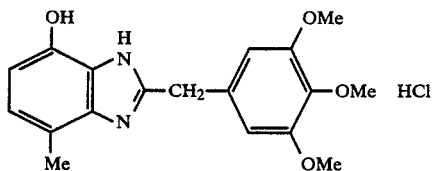

m.p. 250°–1° C. (dec) (ethanol-ether)
Anal. $C_{18}H_{20}N_2O_4 \cdot HCl$ requires C,59.26; H,5.80; N,7.68; Cl,9.72%. Found: C,59.06; H,5.96; N,7.65; Cl,9.96%.

EXAMPLE 26

2-(3',4'-Dimethoxybenzyl)-4-hydroxy-7-methylbenzimidazole hydrochloride

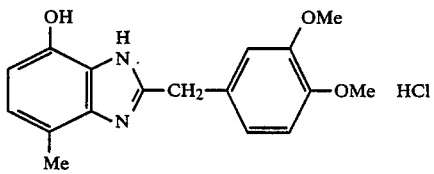

m.p. 264°–5° C. (dec) (ethanol-ether)
Anal. $C_{17}H_{18}N_2O_3 \cdot HCl$ requires C,60.98; H,5.72; N,8.37; Cl.10.59%. Found: C,60.69; H,5.71; N,8.23; Cl,10.78%.

EXAMPLE 27

2-(3'-Methoxybenzyl)-4-hydroxy-7-methylbenzimidazole hydrochloride: Ethanol

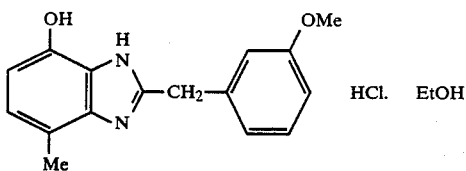

m.p. 239°–241° C. (ethanol-ether)
Anal. $C_{16}H_{16}N_2O_2 \cdot HCl \cdot C_2H_6O$ requires C,61.62; H,6.61; N,7.99%. Found: C,61.91; H,6.70; N,8.02%.

EXAMPLE 28

2-(4'-Methoxyphenyl)-4-hydroxy-7-methylbenzimidazole hydrochloride: ethanol

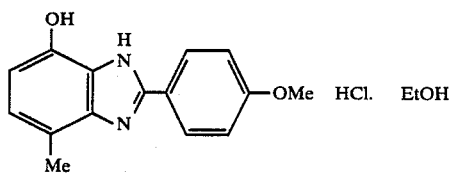

m.p. 283°–5° C. (ethanol-ether)

Anal. $C_{15}H_{14}N_2O_2 \cdot HCl \cdot C_2H_6O$ requires C,60.62; H,6.29; N,8.32; Cl,10.53%. Found: C,60.71; H,6.21; N,8.48; Cl,10.26%. C,60.46; H,6.13; N,8.31; Cl,10.22%

EXAMPLE 29

2-(2'-Methoxybenzyl)-4-hydroxy-7-methylbenzimidazole hydrochloride

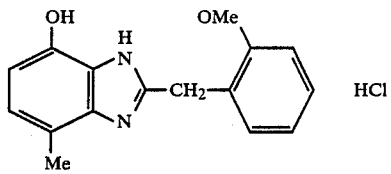

m.p. 244°–245° (ethanol)
Anal: $C_{16}H_{16}N_2O_2 \cdot HCl$ requires C, 63.05; H, 5.62; N, 9.19%. Found: C, 63.02; H, 5.56; N, 9.24%

EXAMPLE 30

2-(4'-Hydroxybenzyl)-4-hydroxy-7-methylbenzimidazole hydrochloride

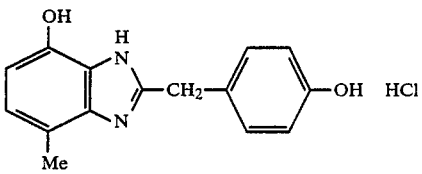

m.p. 273°–5° C. (ethyl acetate)
Anal. $C_{15}H_{14}N_2O_2 \cdot HCl$ requires C,61.96; H,5.20; N,9.64%. Found: C,61.71; H,5.40; N,9.36%.

The following compounds are prepared by analogous methods:

EXAMPLE 31

2-(1-Phenylethyl)-4-hydroxy-7-methylbenzimidazole.

EXAMPLE 32

2-(Thien-2-yl)-4-hydroxy-7-methylbenzimidazole.

EXAMPLE 33

2-(Imidazol-1-yl)methyl-4-hydroxy-7-methylbenzimidazole

EXAMPLE 34

2-Benzyl-3-acetyl-4-hydroxy-7-methylbenzimidazole and 1-acetyl-2-benzyl-4-hydroxy-7-methylbenzimidazole.

EXAMPLE 35

2-Benzyl-4-hydroxy-5-chloro-7-methylbenzimidazole.

EXAMPLE 36

2-n-Hexyl-4-hydroxy-5-tert.-butyl-7-methylbenzimidazole

EXAMPLE 37

2-Benzyl-4-hydroxy-5-tert.-butyl-benzimidazole.

EXAMPLE 38

2-Benzyl-3-acetyl-4-hydroxy-5-chloro-benzimidazole, and 1-acetyl-2-benzyl-4-hydroxy-5-chlorobenzimidazole.

The pharmacological activity of illustrative compounds of this invention was determined using the following methods:

Method A

Rat Adjuvant Arthritis Model

The test is as described by Newbould, Brit. J. Pharmacol., 1963, 21, 127–136.

It is used to indicate anti-rheumatic activity as shown by inhibiting the development of arthritis in the rat adjuvant arthritis model. The compound of Example 1 is active at a concentration of 25 mg/kg (i.p.)

Method B

RBL-1 5-Lipoxygenase Screen

5-Lipoxygenase enzyme was prepared as a 10,000 g supernatant from RBL-1 cells by the method of Jakschik [Jakschik, B. A., F. F. Sun, L. M. Lee, and M. M. Steinhoff, 1980, Biochem. Biophys. Res. Comm. 95, 103]. The 10,000 g supernatant was diluted with homogenization buffer to the equivalent of $1.5-2.5 \times 10^7$ cells. $ml^{-1}$ and made 2 mM with respect to $CaCl_2$. Aliquots of 0.5 ml were then dispensed into tubes, and incubated at 29° C. with 5 μl ethanol or compound in ethanol at the desired concentration for 2 min. Then [1-$^{14}$] arachidonic acid was added in buffer to give final concentration of 6.3 μM and 0.2 μCi per incubation, and the reaction continued at 29° C. for 2 min. The reaction was terminated by adding 1 ml of acetone and cooling on ice, 0.5 ml of ice-cold saline and 10 μl of 2N formic acid were added, and the mixture was extracted with $2 \times 2$ ml of chloroform. The extract was stored under $N_2$ at $-20°$ C. until analysis by chromatography. Activity was measured as the percentage of total radioactivity found in 5-HETE and 5,12-diHETE, and inhibition calculated as the decrease in formation of the sum of these two species in compound-treated incubates relative to control incubates.

This test is used to show inhibition of the 5-lipoxygenase enzyme in a mammalian RBL-1 cell free 5-lipoxygenase assay.

At a 5 μM concentration, the percentage inhibition by the compound of Example 1 was 78.1 ($p<0.001$); while at a 0.5 μM concentration the percentage inhibition was 36.0 ($p<0.01$).

Method C

CARRAGEENIN-INDUCED PLEURISY IN THE RAT

This model of monocyte accumulation is based on the method of R. Vinegar, J. F. Truax, J. L. Selph and F. A. Voelker [Federation Proceedings 41, 2588–2595, 1982].

0.2 ml of a 2.0% solution of λ-carrageenin (Viscarin 402) in saline was injected intrapleurally in anaesthetised rats (wt. approx. 175–200 g). Compounds were administered 1 hour before carrageenin and at 24 and 48 hours after carrageenin. 72 hours after carrageenin injection, 4.0 ml of EDTA solution (5 g EDTA in 100 ml of 0.9% saline and 325 mg phenol red added together with saline to 1 litre) was injected intrapleurally after killing the animals, and the exudate removed with a syringe through the diaphragm. Exudate volume was calculated from the dilution of the phenol red injected, determined spectrophotometrically (560 nm) and cellular content estimated with a DNA assay [Karsten U. and Wollenberger A. Anal. Biochem. 77, 464–470, 1977].

This test is used to indicate anti-inflammatory activity against carrageenin-induced pleurisy in the rat.

The compound of Example 10 was active at a dose of 25 mg/kg (p.o.), the compound of Example 12 at 25 mg/kg (p.o.), and the compound of Example 18 at 12 mg/kg (i.p).

Method D

Rat passive peritoneal anaphylaxis (PPA)

The method is essentially similar to that described previously by Ross et al (Ross, Janet W., Smith, H. and Spicer, Barbara A. Increased vascular permeability during passive peritoneal anaphylaxis in the rat. Int. Arch. Allergy appl. Innum. 51, 226, 1976.)

Animals

Charles River Sprague Dawley male rats of 225–275 g and Dunkin Hartley male white guinea pigs of 300–700 g were used.

Antiserum

Charles River Sprague Dawley male rats of 225–275 g were given intraperitoneal injections of 0.5 ml of either Bordetella pertussis vaccine ($4 \times 10^{10}$ organisms/ml; Burroughs Wellcome, London) or Pertussis vaccine absorbed (not less than 41.u. B. pertussis antigen with aluminium hydroxide; The Lister Institute Elstree, England), and subcutaneous injections of 0.5 ml of an emulsion of 100 mg of ovalbumin (chicken egg albumin; crystallised and lyophilised, grade V, Sigma, London) in 2 ml of isotonic saline and 3 ml of incomplete Freund's adjuvant. The rats were bled by cardiac puncture, under ether anaesthesia, on day 18, the blood was pooled and the serum separated, stored at $-20°$ C. and thawed only once before use. The serum produced 72 hour passive cutaneous anaphylaxis activity in recipient rats to a dilution of 1:64 which was decreased to a dilution of less than 1:2 by heating at 56° C. for 4 hours.

Passive peritoneal anaphylaxis

Rats were given intraperitoneal injections of 2 ml of a 1:5 dilution of the rat anti-serum in isotonic saline. Two hours later 0.3 ml of 5% solution of Pontamine Sky Blue (Raymond A. Lamb, London) in isotonic saline was injected intraveneously, followed by an intraperitoneal injection of the test compound in 1 ml of saline; (control rats received 1 ml of saline); followed 2.5 minutes later by an intraperitoneal injection of 5 ml of a Tyrode solution containing 50 μg/ml heparin and 0.4 mg/ml of ovalbumin. The concentrations of the compounds were quoted as that in the 6 ml of fluid injected intraperitoneally. Exactly 5 minutes after challenge the rats were stunned and bled and their peritoneal fluids were collected by opening their peritoneal cavities over funnels into polycarbonate tubes in ice. The supernatants were separated from the cellular residue by centrifuging at 150 g for 5 minutes and any samples obviously contaminated with blood were discarded for estimation of dye, histamine and SRS-A. Groups of at least 5 rats were used for each dose of compound and the treatments were randomized.

Assay of peritoneal fluids

Collected peritoneal fluids were immediately cooled to 0° C. and centrifuged and the supernatant fluids were placed in a boiling water bath for 5 minutes and stored frozen at −20° C. until assayed for SRS-A.

SRS-A Assay

SRS-A was assayed on the isolated guinea pig ileum preparation in the presence of atropine ($5 \times 10^{-7}$M) and mepyramine maleate ($10^{-6}$M), the latter to abolish the histamine response. (Brocklehurst, W. E. The release of histamine and formation of a slow reacting substance (SRS-A) during anaphylactic shock. J. Physiol., Lond. 151, 416, 1960). Bulked peritoneal fluids from passively sensitised and challenged rats were centrifuged, heated, stored at −20° C. in 0.5 ml aliquots, and used as a reference SRS-A standard, and arbitrarily designated as containing 10 Units per ml. Concentrations of the unknown were bracketed by reference SRS-A samples. At the concentrations used, the compounds tested did not interfere with the assay.

Results

The results obtained in this test are shown in the following table and demonstrate the ability of the compounds of Examples 12, 25 and 26 to inhibit the release of SRS-A in this in vivo system. All compounds were given at a final concentration of $2 \times 10^{-4}$M.

| Example No. | % inhibition of SRS-A release compared to controls |
|---|---|
| 12 | 58 |
| 25 | 59 |
| 26 | 55 |

No toxic effects were observed during any of these test procedures.

We claim:

1. A method of treatment or prophylaxis of inflammatory conditions in mammals which comprises administering to the sufferer an effective amount of a compound of formula (I);

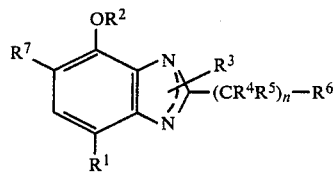

or a pharmaceutically acceptable salt thereof, in which $R^1$ represents hydrogen or a lower alkyl group, $R^2$ represents hydrogen, a lower alkyl group, or

$R^3$ represents hydrogen, a lower alkyl group, or

$R^4$ represents hydrogen or a lower alkyl group,
$R^5$ represents hydrogen or a lower alkyl group,
$R^6$ represents hydrogen, a lower alkyl group, a carbocyclic or heterocyclic aryl group, or —COOR$^{15}$,
$R^7$ represents hydrogen, halogen or a lower alkyl group,
$R^8$ represents a lower alkyl group or a carbocyclic aryl group,
$R^{15}$ represents hydrogen or a lower alkyl group, and n is 0 to 8, n being 0 when $R^6$ represents lower alkyl, wherein said carbocyclic aryl group is selected from groups of the formulae:

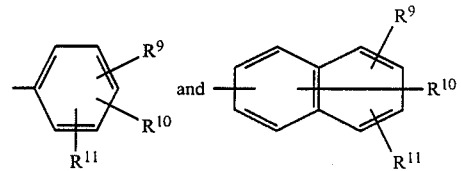

wherein $R^9$, $R^{10}$, and $R^{11}$ independently represent hydrogen, hydroxy, lower alkoxy, lower alkyl, halogen, trifluoromethyl, nitrile, nitro, amino, NR$^{12}$R$^{13}$ (wherein $R^{12}$ and $R^{13}$ are independently hydrogen or lower alkyl), —COOH, —COOR$^{14}$,

or

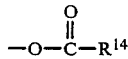

(wherein $R^{14}$ is lower alkyl), or wherein $R^9$ and $R^{10}$ are linked and together represent methylenedioxy or $C_3$-$C_4$ alkylene, and wherein said heterocyclic aryl group is selected from groups of the formulae:

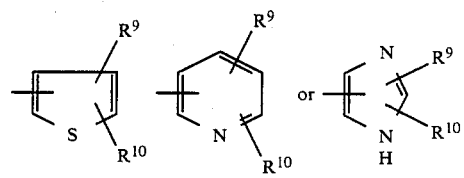

wherein $R^9$ and $R^{10}$ are as defined above.

2. A method of treatment or prophylaxis of allergic conditions in mammals which comprises administering to the sufferer an effective amount of a compound of formula (I):

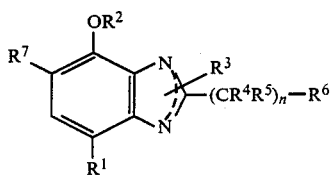

or a pharmaceutically acceptable salt thereof, in which
R$^1$ represents hydrogen or a lower alkyl group,
R$^2$ represents hydrogen, a lower alkyl group, or

R$^3$ represents hydrogen, a lower alkyl group, or

R$^4$ represents hydrogen or a lower alkyl group,
R$^5$ represents hydrogen or a lower alkyl group,
R$^6$ represents hydrogen, a lower alkyl group, a carbocyclic or heterocyclic aryl group, or —COOR$^{15}$,
R$^7$ represents hydrogen, halogen or a lower alkyl group,
R$^8$ represents a lower alkyl group or a carbocyclic aryl group,
R$^{15}$ represents hydrogen or a lower alkyl group, and n is 0 to 8, n being 0 when R$^6$ represents lower alkyl, wherein said carbocyclic aryl group is selected from groups of the formulae:

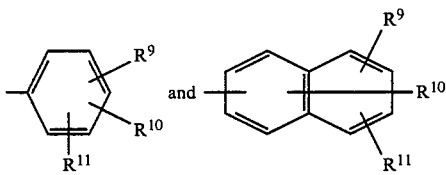

wherein R$^9$, R$^{10}$, and R$^{11}$ independently represent hydrogen, hydroxy, lower alkoxy, lower alkyl, halogen, trifluoromethyl, nitrile, nitro, amino, NR$^{12}$R$^{13}$ (wherein R$^{12}$ and R$^{13}$ are independently hydrogen or lower alkyl), —COOH, —COOR$^{14}$,

or

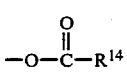

(wherein R$^{14}$ is lower alkyl), or wherein R$^9$ and R$^{10}$ are linked and together represent methylenedioxy or C$_3$–C$_4$ alkylene, and wherein said heterocyclic aryl group is selected from groups of the formulae:

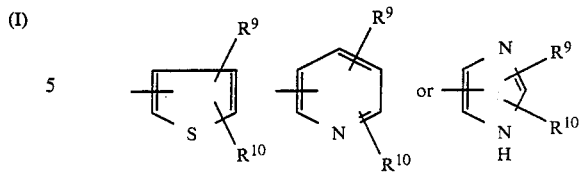

wherein R$^9$ and R$^{10}$ are as defined above.

3. A method of treatment or prophylaxis of loss of gastro-intestinal integrity in mammals which comprises administering to the sufferer an effective amount of a compound of formula (I):

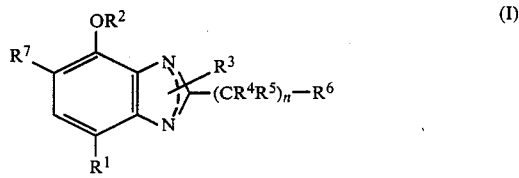

or a pharmaceutically acceptable salt thereof, in which
R$^1$ represents hydrogen or a lower alkyl group,
R$^2$ represents hydrogen, a lower alkyl group, or

R$^3$ represents hydrogen, a lower alkyl group, or

R$^4$ represents hydrogen or a lower alkyl group,
R$^5$ represents hydrogen or a lower alkyl group,
R$^6$ represents hydrogen, a lower alkyl group, a carbocyclic or heterocyclic aryl group, or —COOR$^{15}$,
R$^7$ represents hydrogen, halogen or a lower alkyl group,
R$^8$ represents a lower alkyl group or a carbocyclic aryl group,
R$^{15}$ represents hydrogen or a lower alkyl group, and n is 0 to 8, n being 0 when R$^6$ represents lower alkyl, wherein said carbocyclic aryl group is selected from groups of the formulae:

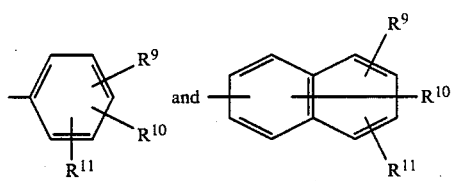

wherein R$^9$, R$^{10}$, and R$^{11}$ independently represent hydrogen, hydroxy, lower alkoxy, lower alkyl, halogen, trifluoromethyl, nitrile, nitro, amino, NR$^{12}$R$^{13}$ (wherein R$^{12}$ and R$^{13}$ are independently hydrogen or lower alkyl), —COOH, —COOR$^{14}$,

or

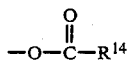

(wherein $R^{14}$ is lower alkyl), or wherein $R^9$ and $R^{10}$ are linked and together represent methylenedioxy or $C_3$–$C_4$ alkylene, and wherein said heterocyclic aryl group is selected from groups of the formulae:

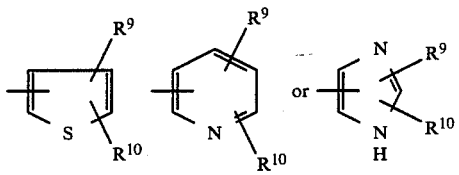

wherein $R^9$ and $R^{10}$ are as defined above.

4. A method according to claim 1 wherein said composition is in a form selected from the group consisting of tablets, capsules, sachets, iozenges, reconstitutable powders, suppositories, emulsions, syrups, elixirs, snuff, aerosols, nebulizer solutions, microfine powders for insufflation, ointments, creams, lotions, gels and skin paints for topical applications.

5. A method according to claim 2 wherein said composition is in a form selected from the group consisting of tablets, capsules, sachets, lozenges, reconstitutable powders, suppositories, emulsions, syrups, elixirs, snuff, aerosols, nebulizer solutions, microfine powders for insufflation, ointments, creams, lotions, gels and skin paints for topical applications.

6. A method according to claim 3 wherein said composition is in a form selected from the group consisting of tablets, capsules, sachets, lozenges, reconstitutable powders, suppositories, emulsions, syrups, elixirs, snuff, aerosols, nebulizer solutions microfine powders for insufflation, ointments, creams, lotions, gels and skin paints for topical applications.

* * * * *